US008657822B2

(12) United States Patent
Bake et al.

(10) Patent No.: US 8,657,822 B2
(45) Date of Patent: Feb. 25, 2014

(54) SURGICAL KIT FOR CARTILAGE REPAIR COMPRISING IMPLANT AND A SET OF TOOLS

(75) Inventors: Nina Bake, Lidingö (SE); Leif Ryd, Stockholm (SE); Morgan Andersson, Lit (SE); Mats Andersson, Lerum (SE)

(73) Assignee: Episurf IP-Management AB, Stockholm (SE)

( * ) Notice: Subject to any disclaimer, the term of this patent is extended or adjusted under 35 U.S.C. 154(b) by 0 days.

(21) Appl. No.: 13/699,150

(22) PCT Filed: May 24, 2011

(86) PCT No.: PCT/EP2011/058473
§ 371 (c)(1),
(2), (4) Date: Mar. 18, 2013

(87) PCT Pub. No.: WO2011/147831
PCT Pub. Date: Dec. 1, 2011

(65) Prior Publication Data
US 2013/0172891 A1  Jul. 4, 2013

Related U.S. Application Data

(60) Provisional application No. 61/347,655, filed on May 24, 2010.

(30) Foreign Application Priority Data

May 24, 2010 (EP) .................................. 10163705

(51) Int. Cl.
*A61B 17/17* (2006.01)
*A61B 17/16* (2006.01)
(52) U.S. Cl.
USPC .......................................................... 606/80

(58) Field of Classification Search
USPC ................................ 606/80–85, 86 R, 96–99
See application file for complete search history.

(56) References Cited

U.S. PATENT DOCUMENTS

| 5,766,221 A | 6/1998 | Benderev et al. |
| 5,938,686 A | 8/1999 | Benderev et al. |

(Continued)

FOREIGN PATENT DOCUMENTS

| EP | 1277450 A2 | 1/2003 |
| EP | 1 698 307 | 9/2006 |

(Continued)

OTHER PUBLICATIONS

U.S. Appl. No. 13/699,090, Bake et al.

(Continued)

*Primary Examiner* — Christopher Beccia
(74) *Attorney, Agent, or Firm* — Drinker Biddle & Reath LLP

(57) ABSTRACT

A surgical kit for cartilage repair at an articulating surface of a joint, including a medical implant and a set of tools. The medical implant includes a substantially plate shaped implant body having a predetermined cross-section that substantially corresponds to the area of the damaged cartilage. The set of tools includes a guide tool including a positioning body and a guide channel. The positioning body has a cartilage contact surface that has a shape and contour that is designed to correspond to and to fit the contour of the cartilage or subchondral bone in the joint in a predetermined area surrounding the site of diseased cartilage. The guide channel has a cross-sectional profile that is designed to correspond to the cross-section of the plate shaped implant body. Additional tools in the set of tools have a cross-sectional profile that is designed to correspond to the cross-sectional profile of the guide channel.

18 Claims, 15 Drawing Sheets

(56) References Cited

U.S. PATENT DOCUMENTS

| | | | |
|---|---|---|---|
| 6,001,104 A | 12/1999 | Benderev et al. | |
| 6,306,142 B1* | 10/2001 | Johanson et al. | 606/79 |
| 6,626,667 B2 | 9/2003 | Sussman | |
| 7,160,331 B2 | 1/2007 | Cooney, III et al. | |
| 7,258,701 B2 | 8/2007 | Aram et al. | |
| 7,608,110 B2 | 10/2009 | O'Driscoll et al. | |
| 8,241,338 B2 | 8/2012 | Castaneda et al. | |
| 2002/0055783 A1 | 5/2002 | Tallarida et al. | |
| 2002/0082704 A1* | 6/2002 | Cerundolo | 623/20.35 |
| 2003/0065400 A1 | 4/2003 | Beam et al. | |
| 2003/0100947 A1* | 5/2003 | Nadler et al. | 623/11.11 |
| 2003/0216669 A1* | 11/2003 | Lang et al. | 600/587 |
| 2004/0002766 A1 | 1/2004 | Hunter et al. | |
| 2004/0039447 A1* | 2/2004 | Simon et al. | 623/13.11 |
| 2005/0049710 A1 | 3/2005 | O'Driscoll et al. | |
| 2005/0137600 A1* | 6/2005 | Jacobs et al. | 606/79 |
| 2006/0190078 A1 | 8/2006 | Fell | |
| 2007/0021838 A1* | 1/2007 | Dugas et al. | 623/20.3 |
| 2008/0195216 A1* | 8/2008 | Philipp | 623/18.11 |
| 2008/0257363 A1 | 10/2008 | Schoenefeld et al. | |
| 2008/0312659 A1 | 12/2008 | Metzger et al. | |
| 2009/0209962 A1 | 8/2009 | Jamali | |
| 2009/0226068 A1* | 9/2009 | Fitz et al. | 382/131 |
| 2009/0228104 A1 | 9/2009 | Strzepa et al. | |
| 2009/0254093 A1 | 10/2009 | White et al. | |
| 2009/0254367 A1 | 10/2009 | Belcher et al. | |
| 2011/0125277 A1 | 5/2011 | Nygren et al. | |

FOREIGN PATENT DOCUMENTS

| | | |
|---|---|---|
| EP | 1704826 A1 | 9/2006 |
| EP | 2116210 A1 | 11/2009 |
| JP | H8-173523 | 7/1996 |
| JP | 2883214 | 4/1999 |
| JP | 2003-531657 | 10/2003 |
| JP | 2006-510403 | 3/2006 |
| JP | 2008-188400 | 8/2008 |
| JP | 2008-540057 | 11/2008 |
| JP | 2011-517579 | 6/2011 |
| WO | 01/43667 | 6/2001 |
| WO | WO-01/82677 A2 | 11/2001 |
| WO | WO-2004/049981 A2 | 6/2004 |
| WO | WO-2004/075777 A2 | 9/2004 |
| WO | WO-2006/060416 | 6/2006 |
| WO | WO-2006/060416 A2 | 6/2006 |
| WO | 2006/091686 | 8/2006 |
| WO | WO 2006/127486 | 11/2006 |
| WO | 2007/014164 | 2/2007 |
| WO | WO-2007/092841 A2 | 8/2007 |
| WO | 2008/098061 | 8/2008 |
| WO | 2008/101090 | 8/2008 |
| WO | 2009/108591 | 9/2009 |
| WO | 2009/111626 | 9/2009 |
| WO | WO-2009/106816 | 9/2009 |
| WO | WO-2009/111624 | 9/2009 |
| WO | WO-2009/135889 A1 | 11/2009 |
| WO | WO-2010/114578 A1 | 10/2010 |

OTHER PUBLICATIONS

U.S. Appl. No. 13/699,084, Bake et al.
U.S. Appl. No. 13/699,126, Bake et al.
English translation of a Summary of a Notice of Reasons for Rejection issued in corresponding Japanese patent application No. 2013-511656 dated Apr. 30, 2013 (1 page).
English translation of a Japanese Office Action dated Jun. 4, 2013 issued in Japanese patent application No. 2013-511657 (2 pages).
Notice of Reasons for Rejection dated Apr. 30, 2013 issued in corresponding Japanese patent application No. 2013-511655 (with English summary thereof) (3 pages).

* cited by examiner

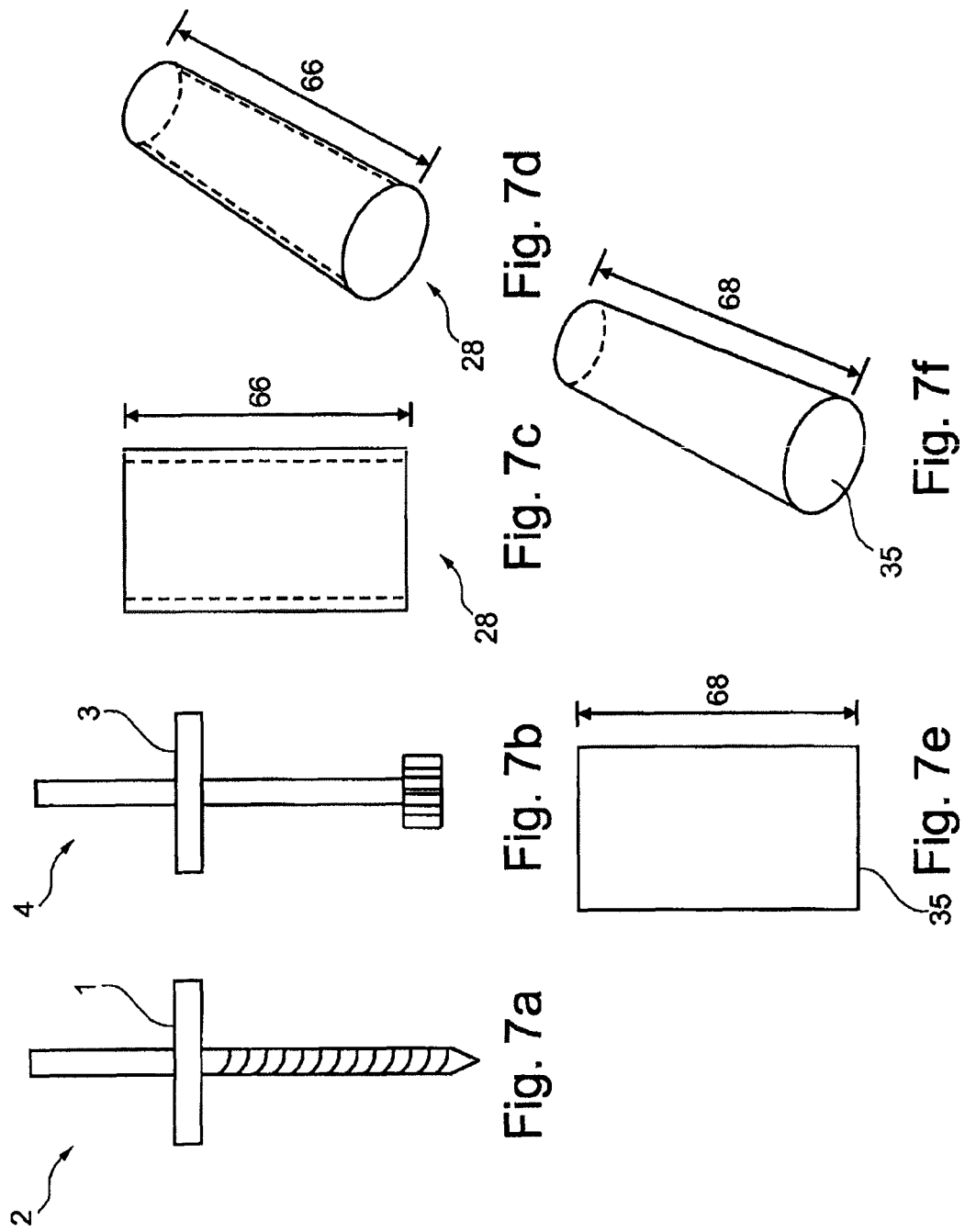

SURGICAL KIT FOR CARTILAGE REPAIR COMPRISING IMPLANT AND A SET OF TOOLS

CROSS REFERENCE TO RELATED APPLICATIONS

This application is a §371 National Stage Application of PCT International Application No. PCT/EP2011/058473 filed May 24, 2011, and claims priority under 35 U.S.C. §119 and/or §365 to U.S. Provisional Application No. 61/347,655 filed May 24, 2010 and European Patent Application No. 10163705.6 filed May 24, 2010, each of which are herein incorporated by reference in their entirety.

FIELD OF THE INVENTION

This invention relates in general to the field of orthopedic surgery and to surgery kits, kits of tools and medical implants. More particularly the present invention relates to a surgery kit comprising a kit of tools and a medical implant for replacement of damaged cartilage at an articular surface in a joint such as a knee, hip, toe and shoulder.

BACKGROUND

General Background

Pain and overuse disorders of the joints of the body is a common problem. For instance, one of the most important joints which are liable to wearing and disease is the knee. The knee provides support and mobility and is the largest and strongest joint in the body. Pain in the knee can be caused by for example injury, arthritis or infection. The weight-bearing and articulating surfaces of the knees, and of other joints, are covered with a layer of soft tissue that typically comprises a significant amount of hyaline cartilage. The friction between the cartilage and the surrounding parts of the joint is very low, which facilitates movement of the joints under high pressure. The cartilage is however prone to damage due to disease, injury or chronic wear. Moreover it does not readily heal after damages, as opposed to other connective tissue, and if healed the durable hyaline cartilage is often replaced by less durable fibrocartilage. This means that damages of the cartilage gradually become worse. Along with injury/disease comes a problem with pain which results in handicap and loss of function. It is therefore important to have efficient means and methods for repairing damaged cartilage in knee joints.

Today's knee prostheses are successful in relieving pain but there is a limit in the lifetime of the prostheses of 10-15 years. The surgical operation is demanding and the convalescence time is often around 6-12 months. In many cases today, surgery is avoided if training and painkillers can reduce the pain. Prostheses are therefore foremost for elderly patients in great pain, at the end of the disease process; a totally destroyed joint. There are different kinds of prostheses, such as half prosthesis, total prosthesis and revision knee, the latter used after a prosthesis failure. The materials used in today's knee prostheses are often a combination of a metal and a polymeric material, but other materials such as ceramics have also been used. The size of knee prostheses makes it necessary to insert them through open surgery.

Other attempts practiced at various clinics around the world with the main objective to repair or rebuild cartilage include biological approaches such as micro fractures, cartilage cell transplantation (ACI), periost flap, and mosaic plasty surgery. All treatments have shown only limited results, with implications such as high cost, risk of infection, risk of loosening, limited suitability for patients of different ages and the extent and location of damage.

The advantages of implants have stimulated a further development of smaller implants that can be implanted with less invasive surgery. In this development there has also been an effort to achieve small joint implants, suitable for repair of a small cartilage injury that have a minimal influence on the surrounding parts of the joint. In the current development, such small implants are designed with an implant body that may be formed as a thin plate with a hard surface for facing the articulate side of the joint and a bone contacting surface for facing the bone below the damaged part of cartilage. The shape and the curvature of the articulate surface of the implant may be designed to be similar to the shape and the curvature of the part of the joint where the implant is inserted. Such implants are designed as mushrooms with an implant body or head and optionally with a peg or a rod projecting from the bone contacting side of the implant body for fastening the implant to the bone.

SPECIFIC BACKGROUND

In the surgical operation of implanting such small implants it is critical that the implant is positioned in a precise manner. If the implant is offset from its intended position it may cause increased wear or load on the joint. For example, if the implant is tilted this may result in an edge that projects above the cartilage surface and causes wear on the opposing cartilage in the joint. Another example is when the implant is placed in a position with the surface of the implant projecting above the surface of the cartilage causing the joint to articulate in an uneven manner and increasing the load on an opposing point of the joint. For the patient, also small misplacements or deviations from an ideal position may result in pain, longer time for convalescence or even a surgical operation being done in vain and making it more difficult to repair the damage in the joint. A large burden is therefore placed on the surgeon not to misplace or misfit the implant. There is therefore a need for well fitting, customized implants as well as tools that are designed to guide and support the surgeon during the implant surgery.

PRIOR ART

Examples of prior art disclosing smaller implants and tools for replacement of damaged cartilage are shown in:

WO2007/014164 A2 describes a kit comprising a plurality of small joint implants having different predetermined shapes described as circle, oval, L-shape and triangular shape and tools for placing the implants and a method for placing the implant in a joint, e.g. in the knee or other joints where there is a need for repair of a cartilage and/or bone damage. In this piece of prior art each implant shape has a specific guide tool which corresponds to the shape of the implant.

The cartilage damage is repaired by choosing the most suitable implant from the different shapes mentioned above. The corresponding guide tool is selected and is used for faster reaming of the area where the implant is to be placed. A drill is used for drilling a hole to accept the post extending from the bone contacting side of the implant. In the end, the implant is placed on the area reamed or drilled out for the implant. Although it is the intention that the guide tool shall be used for the preparation of the placement of the implant it is also said that the use of the guide tool is optional, see passage sections [019, 020].

US20030216669 A1 Shows methods and compositions for producing articular repair material used for repairing an articular surface. The method for designing an articular implant comprises; taking a image of the joint, reconstructing dimensions of the diseased cartilage surface to correspond to normal cartilage and designing the medical implant accordingly. This prior art also shows a surgical assistance device or surgical tool for preparing the joint to receive an implant. The surgical tool comprises of one or more surfaces or members that conform to the shape of the articular surfaces of the joint. It can include apertures, slots and/or holes that can accommodate surgical instruments such as drills and saws. (see claim 18, [0029], [175] FIG. 13, 15, 16), and thus may also be designed and used to control drill alignment, depth and width, for example when preparing a site to receive an implant [0179]. The tool may be single-use or reusable [181]. These surgical tools (devices) can also be used to remove an area of diseased cartilage and underlying bone or an area slightly larger than the diseased cartilage and underlying bone [0182].

WO2008098061 A2 also shows examples of small articular surface implants and tools for placement of the implants. The tools and the implant are used to repair damaged articular cartilage areas.

WO2006091686 A2 Shows a small implant for replacing a portion of an articular surface (see the abstract). The implant is placed using a rotating excision tool (see page 8 line 25) and the implant is selected from a set (see page to line 22-23).

WO 2009111626 Shows implants for altering wear patterns of articular surfaces of joints (see [00190]) and a device and a method for repair of articular surfaces, in for example a knee. The implants and methods may replace all or a portion of the articular surface and achieve an anatomic or near anatomic fit with the surrounding structures and tissues, the techniques described herein allow for the customization of the implant to suit a particular subject, the implant is a mirror image of the articular surface, see [0057]-[0058]. The implants are selected from predetermined shaped and their location can be optimized for the patients wear pattern and the wear patterns are assessed by for example MRI [0061]-[0063], [0072]. The tools used for placement of the implants are selected depending on MRI images but not created depending on the images [00211].

WO2008101090 A2 shows a method for making a large implant suitable for a joint. The 3D surface of the joint implant is determined using MRI or CT depicting the damaged that is to be repaired.

US2006/0198877 A1 shows a medical instrument for autologous chondrocyte transplantation.

WO2009/108591 A1 shows a method and tools for repairing an articular cartilage defect and also an implant.

US6306142B1 shows a system and tools for transplanting a bone plug from a donor site to a recipient site.

US 2003/0100947 A1 shows a device for repairing articular cartilage defects.

OBJECT OF THE INVENTION

General Object

The general object of the invention is to solve the problem of providing an implant for cartilage replacement and means for enabling precision in the insertion and positioning of the implant at an articular surface of a joint.

Partial Problems

The invention further seeks to solve the partial problems of:

Providing a well fitting cartilage replacement implant that is firmly attached in the joint and is well integrated into the surface structure of the joint, in order to generate optimal repair of damaged tissue and cause minimum damage to the surrounding tissue.

Providing means for implanting the cartilage replacement implant into the joint, improving the positioning of the implant in order to generate optimal repair of damaged tissue and cause minimum damage to the surrounding tissue and aiding the surgeon in that positioning.

SUMMARY OF THE INVENTION

The present invention provides a surgical kit and a method for replacing a portion, e.g. diseased area and/or area slightly larger than disease area, of a joint, e.g. cartilage and/or bone, with an implant and a set of tools which achieves a near anatomic fit of the implant with the surrounding structures and tissues.

A first aspect of the invention is a surgical kit for cartilage repair at an articulating surface of a joint. The surgical kit comprises a medical implant, comprising a substantially plate shaped implant body and an extending post having a cross-sectional area, wherein the plate shaped implant body has a predetermined cross-section that preferably substantially corresponds to the area of the damaged cartilage. Further, the surgical kit comprises a set of tools.

The tool set comprises a guide tool equipped with a positioning body and a guide body with a guide channel which goes through said positioning body and said guide body. The positioning body has a cartilage contact surface that is designed to fit the contour of the cartilage or subchondral bone in the joint in a predetermined area surrounding the site of diseased cartilage. The guide channel has a cross-sectional profile that is designed to correspond to the cross-section of the plate shaped implant body. The guide channel has a muzzle on the cartilage contact surface at a position corresponding to the site of the diseased cartilage.

Further, the set of tools comprises one or several insert tools. The insert tool is used inside the guide channel of the guide tool and fits in the guide channel, with a slight tolerance to allow a sliding movement of the insert tool in the guide channel. The insert tool is in different embodiments of the invention provided e.g. as a cartilage cutting tool, a punch, a cartilage cut drill, a drill guide, a reamer guide and/or a hammer tool.

In one embodiment the tool set comprises an insert tool in the shape of a drill guide with a cross-sectional profile that is designed to correspond to the cross-sectional profile of the guide channel with a tolerance enabling the drill guide to slide within the guide channel, and comprising a drill channel for guiding a drill bit, the drill channel being placed in a position that corresponds to the position of the extending post of the medical implant.

In one embodiment the invention further comprises a drill bit with a cross-sectional area that is slightly smaller than the cross-sectional area of the extending post. In one embodiment the drill channel of the drill guide has a cross-sectional area that matches the cross-sectional area of the drill bit with a tolerance enabling the drill bit to slide within the drill channel. In another embodiment the drill bit is equipped with a depth gauge for adjustment of the depth of drilling.

In still another embodiment the tool set comprises an insert tool in the shape of a reamer guide with a cross-sectional profile that is slightly smaller than the cross-sectional profile of the guide channel with a tolerance enabling the reamer guide to slide within the guide channel.

In another embodiment the tool set comprises an insert tool in the shape of a cartilage cutting tool with a cross-sectional profile that is designed to correspond to the cross-sectional profile of the guide channel with a tolerance enabling the cartilage cutting tool to slide within the guide channel. In one embodiment the cartilage cutting tool is a punch having an end with a cutting surface, said end having a recess with a cross-sectional profile that substantially corresponds to the cross-section of the plate shaped implant body. In another embodiment the cutting tool is a cartilage cut drill having a cross-sectional profile that substantially corresponds to the cross-section of the plate shaped implant body.

In a further embodiment the tool set further comprising a reamer bit. The reamer bit may be equipped with a depth gauge for adjustment of the depth of reaming.

Further varieties of the surgical kit comprising any of the following optional, individual or combinable aspects;

The implant body of the implant is substantially flat, having a thickness of approximately 0.5-5 mm.

The contact surface of the positioning body of the guide tool has three contacting points spread out around the guide body, for contacting parts of the joint in order to provide stable positioning of the guide tool in the joint.

The guide channel has a height of 3-10 cm.

The guide channel comprises an orifice leading through the guide body at the foot of said guide body.

In another embodiment the tool set further comprises a hammer tool with a cross-sectional profile that is designed to correspond to the cross-sectional profile of the guide channel with a tolerance enabling the hammer tool to slide within the guide channel.

In another embodiment the surgical kit of the invention further comprises a drill depth adjustment tool In alternative embodiments of the surgical kit of the invention the drill depth adjustment tool further comprises of a drill depth bit and a drill depth assembly holder holding at least one drill depth spacer.

The drill depth spacer of the surgical kit according to the invention may also comprise of several spacers.

BRIEF DESCRIPTION OF THE FIGURES

The present invention will be further explained below with reference to the accompanying drawings, in which:

FIG. 7a-f shows an exemplifying embodiment of a drill, reamer bit, reamer guide and hammer tool according to the present invention.

DETAILED DESCRIPTION OF THE INVENTION

Introduction

This invention concerns a surgical kit for use in orthopedic surgery. A surgical kit according to the invention comprises an implant and a set of tools for the placement of an implant which replaces damaged cartilage in a joint.

Figure 1:
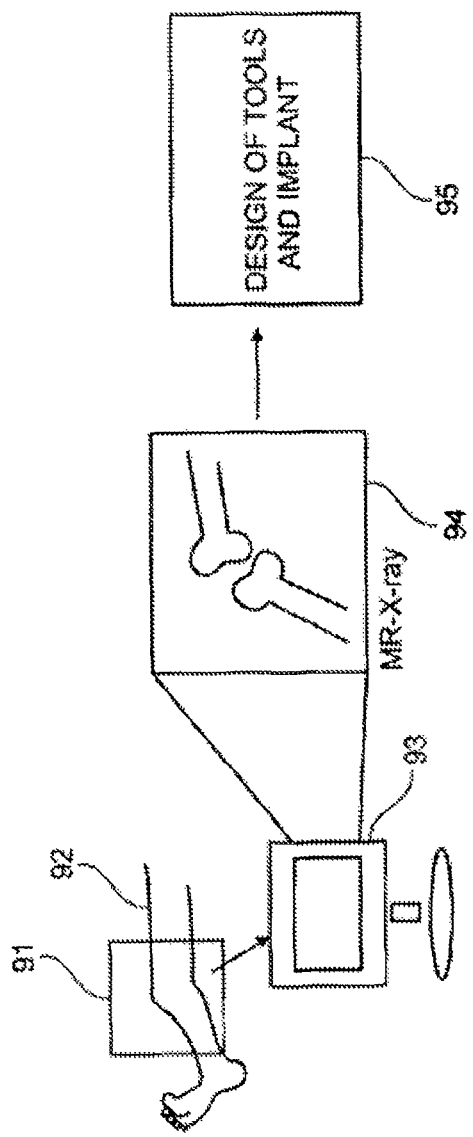
FIG. 1 shows a schematic overview of an exemplifying embodiment of the method in accordance with the invention used for designing a patient specific surgical kit.
Figure 2:
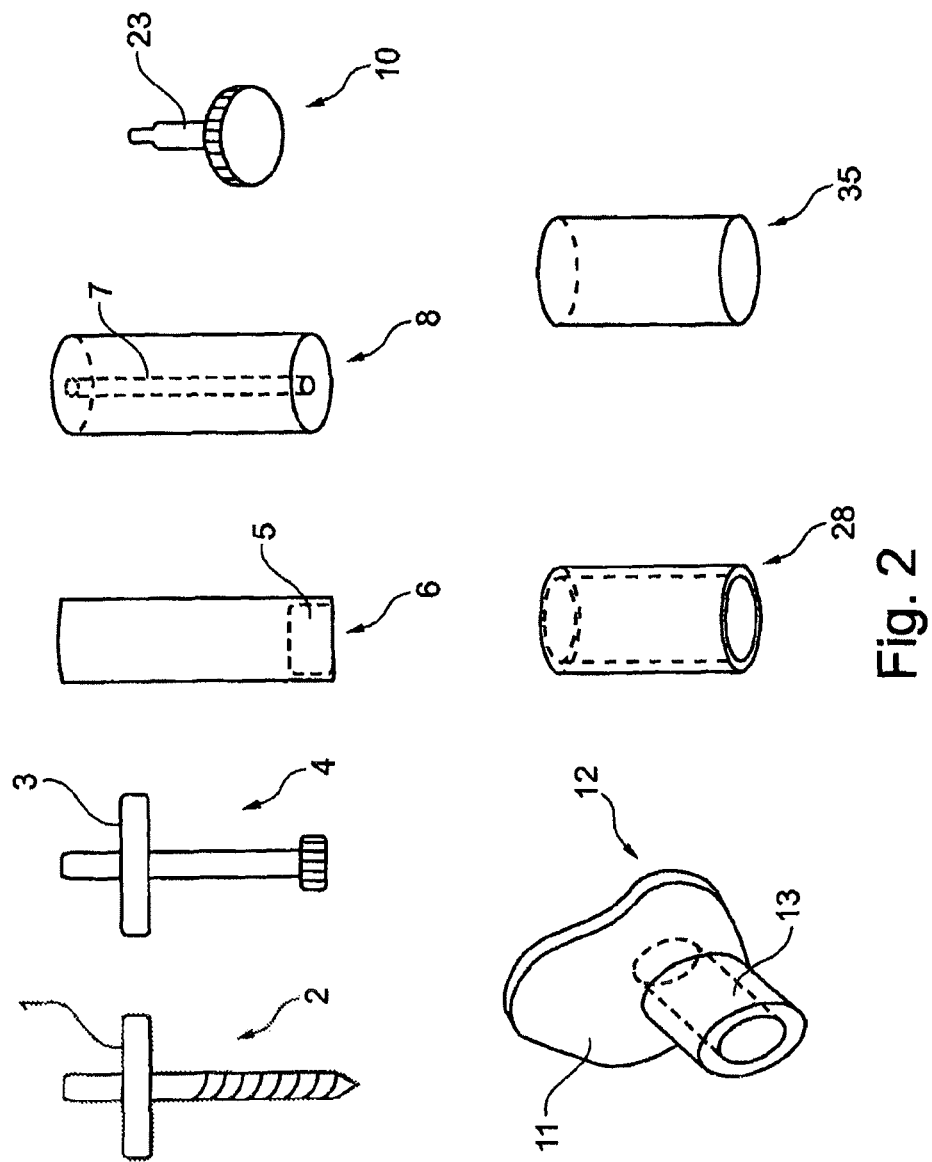
FIG. 2 shows a surgical kit according to one embodiment of the invention, exemplified by a surgical kit for a knee, the surgical kit comprising an implant and a set of tools.

FIG. 2 shows a surgical kit according to one embodiment of the present invention. The surgical kit comprises a, possibly custom made, implant 10 with an extending post 23 and implant adjusted tools; a guide-tool 12, equipped with a guide-channel 13 and a positioning body 11 and a drill guide 8. Further the surgical kit may comprise a cutting tool 6, which in this exemplifying embodiment is a punch, a drill-bit 2, equipped with a depth gauge 1 and/or a reamer-bit 4, equipped with a depth gauge 3, and/or a hammer tool 35 and/or a reamer guide 28 and/or a drill depth adjustment tool 2000.

The implant and the set of tools according to the invention are preferably individually designed for a person's joint. The implant and the set of tools are also optionally individually designed for a specific person's cartilage individual injury.

An exemplifying embodiment of the invention is shown which is especially adapted for cartilage replacement at the femur of a knee joint. The invention may however, also have other useful applications, such as for cartilage replacement at an articulating surface at any other joint in the body, e.g. elbow, ankle, finger, hip, toe and shoulder.

The Surgical Kit

This invention provides a surgical kit where the successful implant insertion is less depending on the skills of the surgeon compared to previously known methods. This invention provides preferably individually designed tools and implant. Due to the design and the function of both tools and implant the surgical kit gives improved implantation precision and a precise desired placement of the implant in the joint every time. The precision of the surgery is "built in" into the design of the tools.

The surgical kit of the invention leads to shorter learning curves for the surgeon since the surgical kit facilitates for quick, simple and reproducible surgery.

In one exemplifying embodiment the implant is intended for replacing damaged cartilage in a knee. The site where the implant is to be implanted according to the invention is an articular cartilage surface including, for example, the lateral femoral chondral (LFC) surfaces, medial femoral chondral (MFC) surfaces, trochlea surfaces, patella surfaces, tibia surfaces (e.g. surfaces of the tuberosities of the tibia), and combinations and portions thereof. For example implants may be placed on any one of these surfaces.

In another exemplifying embodiment the implant is intended for replacing damaged cartilage in a toe, for example on the cartilage surfaces between the metatarsals and the proximal phalanges bones in a toe.

In a further exemplifying embodiment the implant is intended for replacing damaged cartilage in a shoulder, for example on the articulation surfaces between the head of the humerus and the lateral scapula (specifically—the glenoid fossa of the scapula).

The implant is inserted through a small open surgery operation using a tool kit where the tools in the tool kits are preferably individually designed or tailor/custom made for the person who suffers from the injury. This leads to decreased suffering of the patient and is economically favorable since it leads to shorter convalescence time and less time for the patient at the hospital. By using this optionally individually designed surgery kit the implant insertion will be optimal and thus misalignment which is one of the problems associated with the common methods used today can be avoided.

Using the surgical kit according to the invention, small cartilage damages will require small implants and in this way combined with the design of the guide tool, a surgical operation with little tissue damage, a small open surgery, is needed for the person suffering from a knee injury. This gives the effect that minimal modifications on the underlying bone and surrounding tissue are required when preparing for the implant surgery. Using implants according to the present invention makes it possible to repair cartilage defects at a much earlier stage than previously. This early replacement of damaged cartilage may postpone or prevent osteoarthritis.

The object of the invention is to solve the problem of repairing damaged, injured or diseased cartilage in knees, toes, elbows or shoulders by providing an implant that will have better placement and thus a seamless placement in the cartilage.

The benefits from the implant according to the invention are relief from pain and swelling in the joint and also the restoration of a smooth, continuous articulating surface. The implant and the tool kit of the present invention also facilitates for the return to normal activity with rapid recovery time, possibility to postpone or avoid total knee replacement surgery. A less traumatic surgery procedure is used and potentially faster recovery after surgery.

The Implant Structure

Figure 3A:
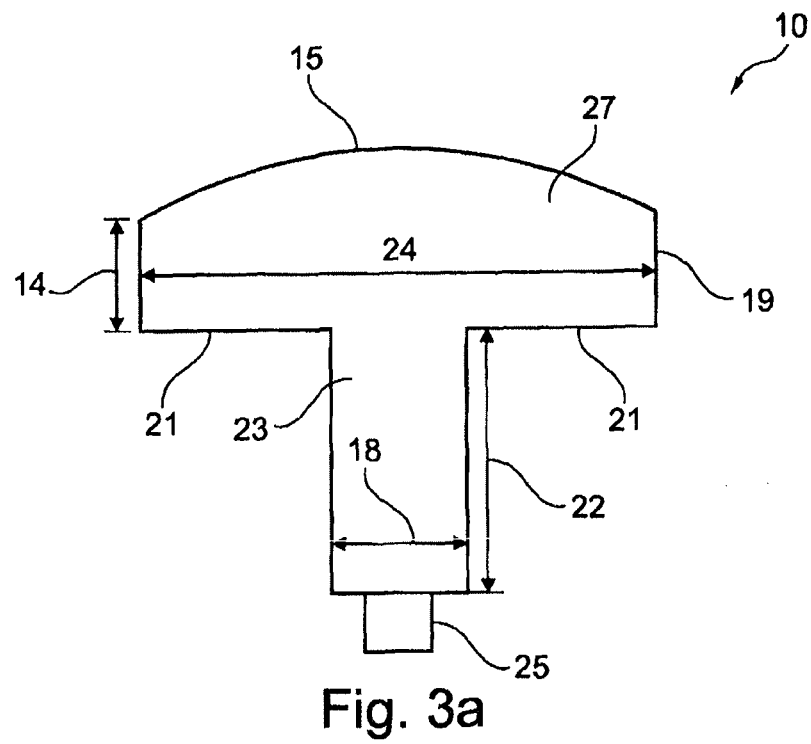
FIG. 3 a-b shows an exemplifying embodiment of an implant according to the present invention.
Figure 3B:
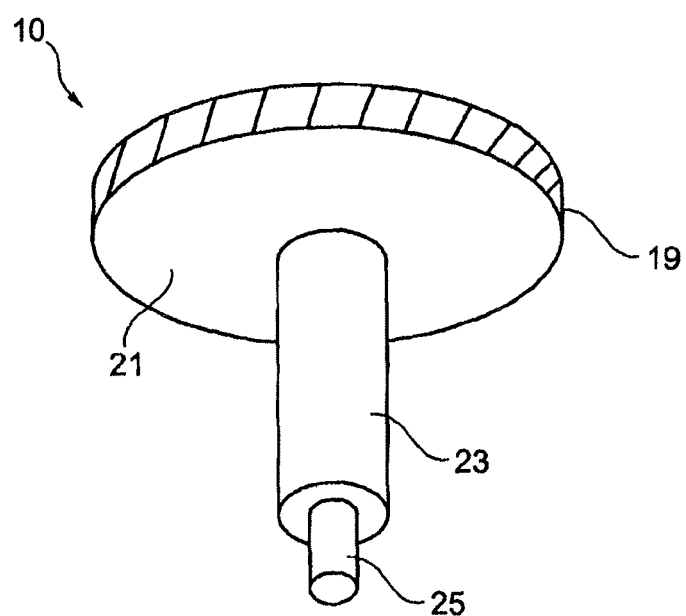

FIG. 3a-3b shows a medical implant 10 of a surgical kit according to an embodiment of the present invention. The plate shaped implant body 27 has an articulate surface (first surface) 15 configured to face the articulating part of the joint and a bone contact surface (second surface) 21 configured to face bone structure in the joint, the plate shaped implant body 27 has a cross-section (see FIG. 8a-b implant (10) with two different cross-sectional views, 81 and 121) that substantially corresponds to the area of the damaged cartilage and the articulate surface 15 has a curvature that optionally substantially corresponds to the curvature of a healthy articulating surface at the site of diseased cartilage. The extending post 23 extends from the bone contact surface 21. Since the implant 10 of the invention is custom made for a specific patient, FIG. 3a-b is an exemplifying schematic picture displaying one embodiments of the implant 10. Between the articulate surface 15 and the bone contact surface 21 there is a cartilage contacting surface 19.

The implant is specially designed, depending on the knees appearance and the shape of the damage and in order to resemble the body's own parts, having a surface which preferably corresponds to a three dimensional (3D) image of a simulated healthy cartilage surface. The implant will be tailor-made to fit each patient's damaged part of the joint.

Implant Body

The implant body 27 is substantially plate shaped, meaning that the shortest distance (represented by 24 in FIG. 3) crossing the surface 15 of the implant body 27 is substantially larger, e.g. at least 1.5 times larger than the thickness 14 of the implant body 27. By substantially plate shaped is meant that the implant body 27 may be substantially flat or may have some curvature, preferably a 3D curvature of the articulate surface 15. The articulate surface 15 may for example have a curvature that corresponds to a simulated healthy cartilage reconstructed from an image taken with MRI image or the CT-scanning of the damaged cartilage surface of the joint. Once the implant 10 is placed in the joint there will be a surface with no parts of the implant pointing up from or down below the surrounding cartilage—the implant is incorporated to give a smooth surface.

The area and the shape of the implant surface 15 are individual depending on the size of cartilage damage and location of the cartilage damage. The area and shape of the implant can be decided by the surgeon himself or be chosen from predetermined shapes. For instance the cross-section of the implant body 27 may have a circular or roughly circular, oval, triangular, square or irregular shape, preferably a shape without sharp edges (see FIG. 8 a-b and implant 10). The implant head or implant body 27 can vary in size and shape and are adjusted to the size and shape of the damaged cartilage tissue and to the needs of particular treatment situations. The size of the implant 10 may also vary. The area of the articulate surface 15 of the implant varies in different realizations of the invention between 0.5 $cm^2$ and 20 $cm^2$, between 0.5 $cm^2$ and 15 $cm^2$, between 0.5 $cm^2$ and 10 $cm^2$, between 1 $cm^2$ and 5 $cm^2$ or preferably between about 0.5 $cm^2$ and 5 $cm^2$.

In general, small implants are preferred since they have a smaller impact on the joint at the site of incision and are also more easily implanted using arthroscopy or smaller open surgical procedures. The primary factor for determining the size of the implant is however the nature of the lesion to be repaired.

The articulate surface 15 of the implant body 27, and the core of the implant body 27, comprises a biocompatible metal, metal alloy or ceramic. More specifically it can comprise any metal or metal alloy used for structural applications in the human or animal body, such as stainless steel, cobalt-based alloys, chrome-based alloys, titanium-based alloys, pure titanium, zirconium-based alloys, tantalum, niobium and precious metals and their alloys. If a ceramic is used as the biocompatible material, it can be a biocompatible ceramic such as aluminium oxide, silicon nitride or yttria-stabilized zirconia. Preferably the articulate surface 15 comprises a cobalt chrome alloy (CoCr) or stainless steel, diamond-like carbon or a ceramic. The articulate surface 15 and the core of the implant body 27 may comprise the same or different materials.

The articulate surface 15 may also be further surface treated in order to e.g. achieve an even more durable surface or a surface with a lower friction coefficient. Such treatments may include, for example, polishing, heat treatment, precipitation hardening or depositing a suitable surface coating.

The Bone Contact Surface

The implant body 27 has a bone contact surface (bone contact surface) 21, configured to face or contact the bone structure of the joint. In one embodiment the bone contact surface 21 comprises a biocompatible metal, metal alloy or ceramic, such as any of the metals, metal alloys or ceramic described above for the articulate surface 15. Preferably the bone contact surface 21 comprises a cobalt chrome alloy (CoCr), a titanium alloy, titanium or stainless steel.

In one embodiment the bone contact surface 21 comprises, or in one specific embodiment is coated with, a bioactive material. In an alternative embodiment of the invention the bone contact surface does not comprise a bioactive material and/or is uncoated.

The bioactive material of the bone contact surface, if present, preferably stimulates bone to grow into or onto the implant surface. Several bioactive materials that have a stimulating effect on bone growth are known and have been used to promote adherence between implants and bone. Examples of such prior art bioactive materials include bioactive glass, bioactive ceramics and biomolecules such as collagens, fibronectin, osteonectin and various growth factors. A commonly used bioactive material in the field of implant technology is the bioactive ceramic hydroxyapatite (HA), chemical formula $Ca_{10}(PO_4)_6(OH)_2$. HA is the major mineral constituent of bone and is able to slowly bond with bone in vivo. HA coatings have been developed for medical implants to promote bone attachment. Another bioactive material commonly used in prior art is bioactive glass. Bioactive glasses, generally comprising $SiO_2$, $CaSiO_3$, $P_2O_5$, $Na_2O$ and/or $CaO$ and possibly other metal oxides or fluorides, are able to stimulate bone growth faster than HA.

The bioactive materials described above have an anabolic effect on the bone i.e. stimulates bone growth. The fixation of the implant can also be improved by decreasing the catabolic processes i.e. decrease the amount of bone resorption next to the implant. The bone contact surface 21 and/or the extending post can also be modified with bisphosphonates. Bisphosphonates are substances that decrease the catabolic process of bone and binds readily to HA. One way to bind the bisphosphonate to the surface is by coating it with HA, which it readily binds to. The implant can also simply be immersed in a bisphosphonate solution or linked with some other biocompatible molecule e.g. carbodiimides, N-hydroxysuccinimide (NHS)-esters, fibrinogen, collagen etc.

In one embodiment the bone contact surface 21 is coated with a double coating. Such double coating may for instance comprise an inner coating comprising titanium (Ti). The second, outer coating, that is configured to contact the cartilage and or bone, is preferably a hydroxyapatite and/or beta tricalcium phosphate (TCP) coating containing more than 95% hydroxyl apatite or 95-99.5% hydroxyapatite. By this design even more long-term fixation of the implant is achieved, since bone in- or on-growth to the implant is further stimulated by the titanium, even if the more brittle hyroxyapatite would eventually shed/dissolve.

The bone contact surface may also be further modified with fluoro compounds or acid etching to enhance the bioactivity and the osseointegration of the surface. Another method to facilitate osseointegration is blasting of the bone contact surface.

The Extending Post

The implant replaces an area of damaged cartilage in an articulating surface of a joint. Before the implant is placed in the desired position, the damaged cartilage is removed and also a part of the bone beneath. Furthermore, a hole can be drilled to fit the implant structure. The extending post of the implant or the rod-part 23 of the implant 10, is used for securing the implant 10 in the drilled hole of the bone. The length of the extending post 23, extending from the implant head, is adjusted to a length needed to secure the implant 10 in the bone. The extending post 23 is intended to give a primary fixation of the implant 10; it provides mechanical attachment of the implant 10 to the bone in immediate connection with the surgical operation.

The position of the extending post 23 on the bone contact surface 21 can be anywhere on the bone contact surface 21 or the extending post 23 may have a central position.

The extending post 23 has a physical structure in the form of for example a cylinder or other shapes such as one or more of a small screw, peg, keel, barb or the like.

The extending post 23 can in one embodiment of the invention be coated with a bioactive material, for example a bone stimulating material with single or double coatings and/or, a substance inhibiting bone resorption such as described for the bone contact surface 21 above. The surface of the extending post can also be further modified using e.g. fluoro compounds or acid etching or blasting, to enhance osseointegration of the surface.

In another embodiment of the invention the extending post 23 is uncoated and the extending post may comprise e.g. a metal, metal alloy or ceramic material, such as the metal, metal alloys or ceramic materials described for the articulate surface 15 above.

In one alternative embodiment, the extending post 23 has a positioning part 25, where the positioning part 25 is located distal to the plate shaped implant body 27. The longitudinal symmetry axes of the first part of the extending post 23 and the positioning part 25 coincide. The diameter of the positioning part 25 is smaller than the diameter of the first part of the extending post 23.

The Set of Tools

The set of tools comprises a guide tool with a guide channel and a selection of insert tools for use when mounting the implant on the implant site. The insert tools are in operation inserted in the guide channel 54 of the guide tool 12 and fits in the guide channel 54, with a slight tolerance to allow a sliding movement of the insert tool in the guide channel 54. The cross-sectional profile, and thus the circumferential shape of the insert tool, corresponds to the chosen cross-section 81 or 121 of the implant surface 15 in size and shape (see FIG. 8a-b). The insert tools are in different embodiments of the invention provided in the form of a cartilage cutting tool, a punch, a cartilage cut drill, a drill guide, a reamer guide and/or a hammer tool. The insert tools are used together with further tools such as a drill bit and/or a reamer bit and/or a drill depth adjustment tool 2000.

The Guide-Tool

Figure 4B:
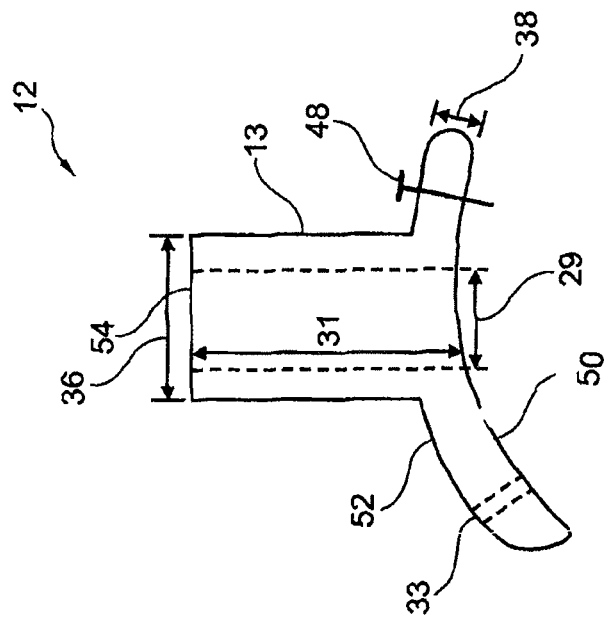
FIG. 4a-b shows an exemplifying embodiment of a guide tool according to the present invention.
Figure 4A:
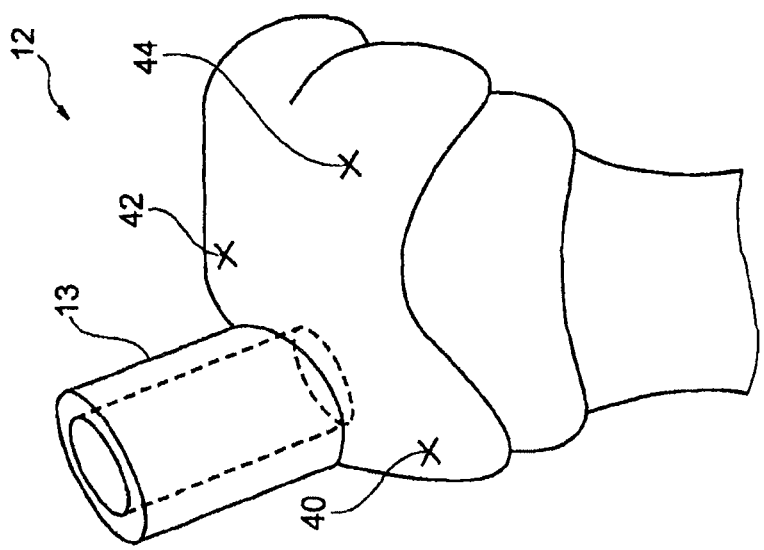
Figure 5B:
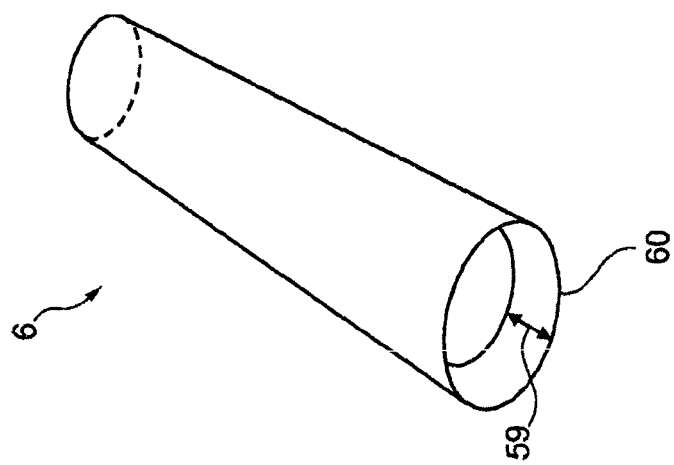
FIG. 5a-b shows an exemplifying embodiment of a cutting tool according to the present invention, a punch.
Figure 5A:
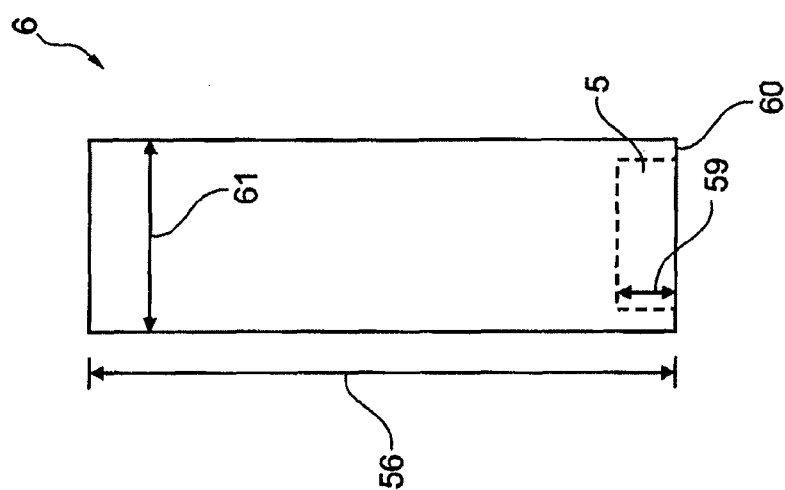
Figure 6B:
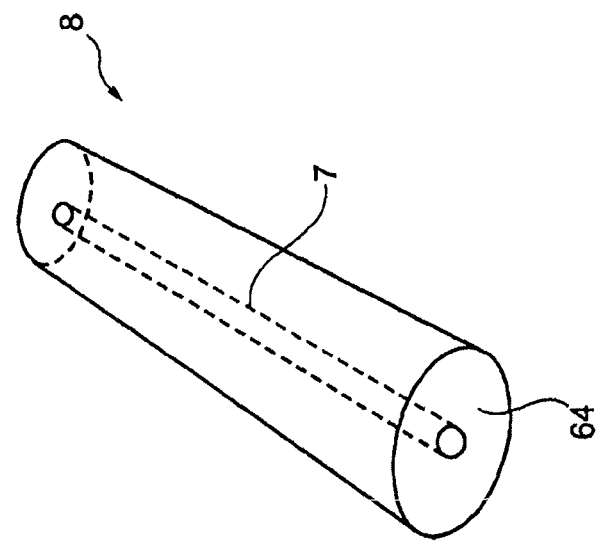
FIG. 6a-b shows an exemplifying embodiment of a drill guide according to the present invention.
Figure 6A:
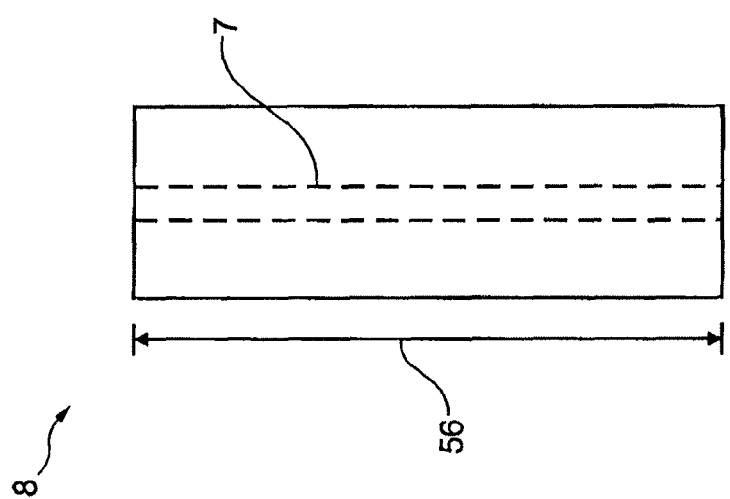

FIGS. 2 and 4a-b shows exemplifying embodiments of a guide-tool 12. The guide tool 12 comprises a positioning body 11 and a guide body 13, with a guide channel 54 through said guide body 13 and positioning body 11. The positioning body has a cartilage contact surface 50 that has a shape and contour that is designed to correspond to and to fit the contour of the cartilage or the subchondral bone in the joint in a predetermined area surrounding the site of diseased cartilage. The guide tool 12 also has a top surface 52 facing the opposite direction compared to the cartilage contacting surface 50. The guide body 13 extends from said top surface 52 of the guide tool 12.

The guide channel 54 has an inner cross-sectional profile 82 or 122 (see FIG. 8a-b) that is designed to correspond to the cross-section 81 or 121 of the plate shaped implant body 10. In other words, the plate shaped implant body 10 fits the guide channel 54, with a slight tolerance to allow a sliding movement of the implant in the guide channel 54. The positioning body 11 has a mouth or muzzle 29 which is the guide channel's 54 opening on the cartilage contact surface 50. The mouth 29 is in a position on the cartilage contact surface 50, corresponding to the site of the diseased cartilage in a joint. The height 31 of the guide channel 54 must be sufficiently long to give support to the tools used inside the guide body 13. The height 31 is preferably higher than the thickness of the surrounding tissue. In this way, the opening of the guide channel 54 is easy to access for the surgeon. The height 31 of the guide channel 54 is between, 1-10 cm, preferably 3-10 cm and always sufficiently high to ensure stabilization of the tools that are to be inserted into the guide channel 54.

The guide tool 12 is easy to place due to the precise fit of the positioning body 11 on the cartilage surface. The guide tool 12 is designed to be inserted in as lesion which is as small as possible to be able to repair the specific cartilage damage. The height 31 of the guide channel 54 is sufficiently high to be easily accessible for the surgeon during surgery. In one embodiment, the top of the guide channel 54 is designed to project above the tissue surrounding the surgery cut when the guide tool is placed on the cartilage in a joint during surgery.

The size and shape of cartilage contact surface 50 of the guide tool 12 is determined depending on the size and shape of the damaged cartilage and thus on the cross section (for example 81) of the implant body 10 and the guide channel 54, and also depending on the position of the cartilage area in a joint. The size and shape of the surface 50 is a consideration between the following aspects; minimize surgery lesion, maximize stability for guide tool 12, anatomic limitations on the site of the injury, not all cartilage surfaces in a joint can be used for placement of the guide tool. A large spread of the cartilage contact surface 50 is to prefer to get good stability of the guide tool, however, a large surface area of the surface 50 may also lead to a large surgical intervention and this is undesired. Thus the size of the cartilage contact surface 50 and of the positioning body 13 is determined by a balance between the desire to achieve good positioning stability and small surgical operations. Also, the cartilage contact surface 50 need not have a continuous, regular shape, but may have an irregular shape, as long as it gives adequate support and stable positioning of the guide tool 12.

When designing the guide tool, the cartilage contact surface 50 can be designed to cover three points (see FIG. 4*a*, 40, 42, 44 for an example) distributed over the cartilage surface of the joint where the implant is to be inserted. The points are chosen to give maximum support and positional stability for the positioning body 11 and thus these points, either decided and identified by the surgeon or automatically identified by design software, serve the ground when designing the surface 50 of the guide tool 12. The cartilage contact surface 50 can also be formed such that it uses the curvature in the cartilage surface in a joint for stability. For example, in a knee joint, the condyles are separated from each other by a shallow depression, the posterior intercondyloid fossa, this curvature together with the medial epicondyle surface can be used to give the cartilage contact surface 50 a stabile attachment to the cartilage surface in a knee joint. The surface is in one embodiment a continuous surface covering a selected area surrounding the cartilage damage. In another embodiment the cartilage contact surface is distributed over a plurality of points, preferably three or more of separated contact points. The cartilage contact surface does not need to be a continuous, regular surface but preferably has at least three points exemplified by 40, 42 and 44 for stability. Optionally the cartilage contacting surface 50 can be further stabilized by attachment with nails, rivets or similar attachment means to the bone surrounding the cartilage in a joint (see FIG. 4*b*). This additional attachment with rivets or the like gives additional support and stability and also gives the possibility to keep the cartilage contact surface as small as possible. The position of the rivets may be predetermined and marked out on the surface 50 by premade drill holes 33.

The guide-tool 12 aids with exact precision removal of a volume of cartilage and subchondral bone and the guide tool 12 also guides the placement of the implant 10 in for example a knee. Placement of the guide-tool 12 on the cartilage surface on a knee can be seen in FIG. 4*a*. The guide tool 12 is manufactured using a suitable material or materials that is/are approved for use in medical procedures, e.g. a ceramic, plastic, metal, metal alloy or aluminia material, or a combination. The guide tool 12, especially the cartilage contact surface 50, is also preferably made of a material that is smooth, even and/or has low friction, in order to lessen the risk of wear and damage to the cartilage on which it is to be placed. Such materials include e.g. metals ceramics and polymers such as acrylonitrile butadiene styrene (ABS). The used materials may further be polished.

Figure 11:
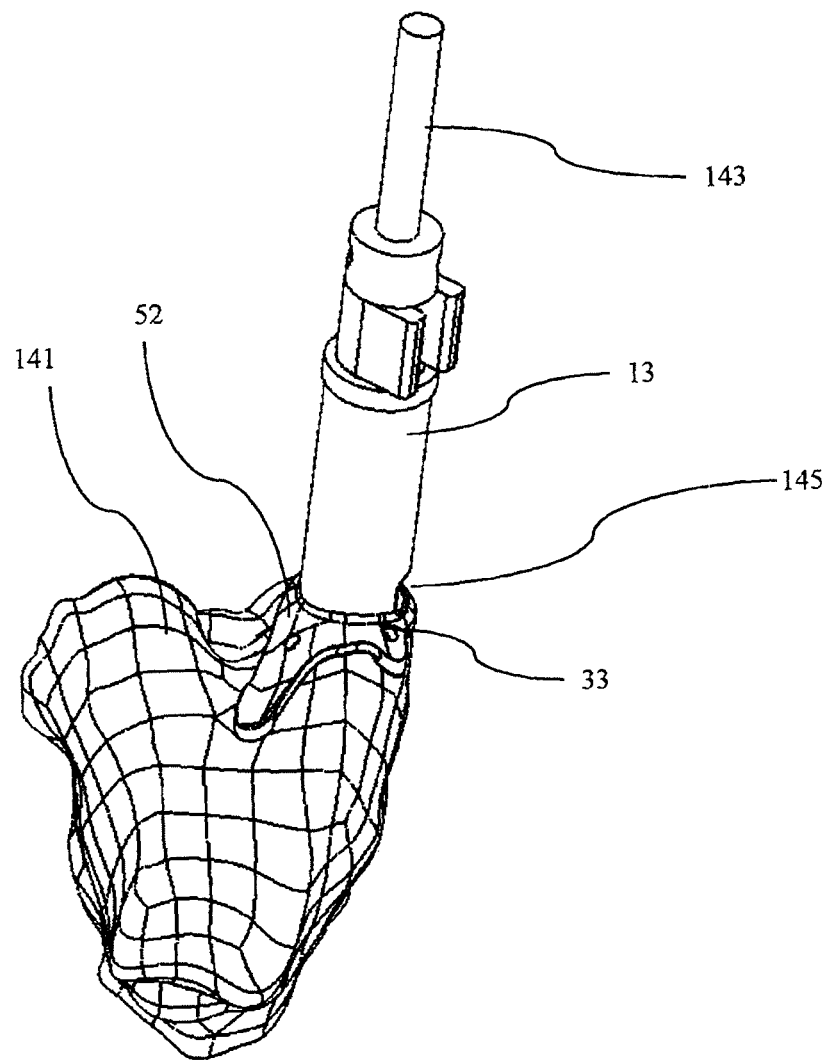
FIG. 11 shows an image of a guide tool designed according to an embodiment of the design method. In this exemplifying embodiment of the guide tool, the guide body comprises an orifice at the foot of the guide body that leads from the guide channel into the open outside the guide body.

FIG. 11 shows an image of a guide tool designed according to an embodiment of the invention. The guide tool is positioned on a representation of a femoral bone 141 over the site of the cartilage damage with its positioning body 11 fitted to the contour of the area surrounding the cartilage damage. A cutting tool 143 such as a bore or a reamer is placed in the guide channel of the guide body. The guide body 13 comprises an orifice 145 at the foot of the guide body that leads from the guide channel into the open outside the guide body. The orifice is designed to enable output of waste such as cartilage tissue and bone chips from boring or reaming in the preparation of the recess for the implant in the joint. The orifice is preferably also designed to enable visual inspection into the implant site during surgical operation.

The Cartilage Cutting Tool

The cartilage cutting tool is a tool which is used to cut the cartilage in the joint around the area of damaged cartilage to prepare for the insertion of the implant. The cartilage cutting tool may for example be a punch 6 or a cartilage cut drill 105, as shown in FIGS. (2, 5*a-b*, 9*b*, 10). It is used inside the guide channel of the guide tool and fits in the guide channel 54, with a slight tolerance to allow a sliding movement of the cartilage cutting tool in the guide channel 54. The cartilage cutting tool preferably cuts the cartilage so that the cut edges of the cartilage are sharp and smooth. These sharp and smooth edges are of great importance when the implant is placed into the prepared recess in the cartilage and bone. In one embodiment the cartilage cutting tool, in addition to cutting the cartilage, may also cut/carve/drill the underlying bone. A hole in the cartilage which is cut (punched or drilled) with the cartilage cutting tool according to the invention ends up with a precise fit of the implant into the prepared cartilage since the cartilage cutting tool allows for an exact, precise cut. The recess in the cartilage and/or bone, made by the cartilage cutting tool always correspond to the chosen cross-section 81 of the implant surface 15 in size and shape (see FIG. 8).

In one exemplifying embodiment of the invention the cartilage cutting tool is a punch 6. The punch 6 is a solid body with a hollow shape or recess 5 in one end. The recess 5 has sharp edges 60. The punch 6 is used to punch out, and remove the damaged cartilage from the joint. The punch is to be placed inside the guide channel 54 of the guide tool 12, with the recess pointing down onto the cartilage. A hammer is then used to hammer the punch recess 5 through the cartilage. In this way the damaged cartilage is removed by punching. The depth 59 of the recess 5 on the punch 6 may be adjusted to the individual person's cartilage thickness. It is of great importance that the punch has sharp cutting edges 60. The material of the punch is chosen from materials which can be formed giving the punch sharp edges of the recess, the material also need to be stable to withstand the pressure when the punch is hammered into the cartilage. Examples of such materials are metals such as stainless steel or ceramic material or a plastic material or a hard coated material. The punch 6 fits the inside of the guide channel 54, see FIG. 8, with a slight tolerance to allow a sliding movement of the punch in the guide channel 54. The fit ensures the correct, desired placement of the punch on the cartilage surface and thus the precise removal of the damaged cartilage area. The punch preferably gives sharp precise edges of the remaining cartilage in the joint surrounding the removed cartilage piece, which is of importance when placing the implant 10 in the joint. The contour of the cutting edge 60, i.e. the contour of the surface of the cutting edge 60 that is to face and cut the cartilage, is in one embodiment designed to match the contour of the patient's cartilage and/or bone at the site of the joint where the punch is to cut. This further ensures that the cartilage will be properly and efficiently cut, giving sharp precise edges of the remaining cartilage as well as minimized damage to the underlying bone.

The length 56 of the punch 6 is in one embodiment longer than the height 31 of the guide channel 54. The length 56 of the punch 6 is preferably between 4 and 12 cm.

Figure 8A:
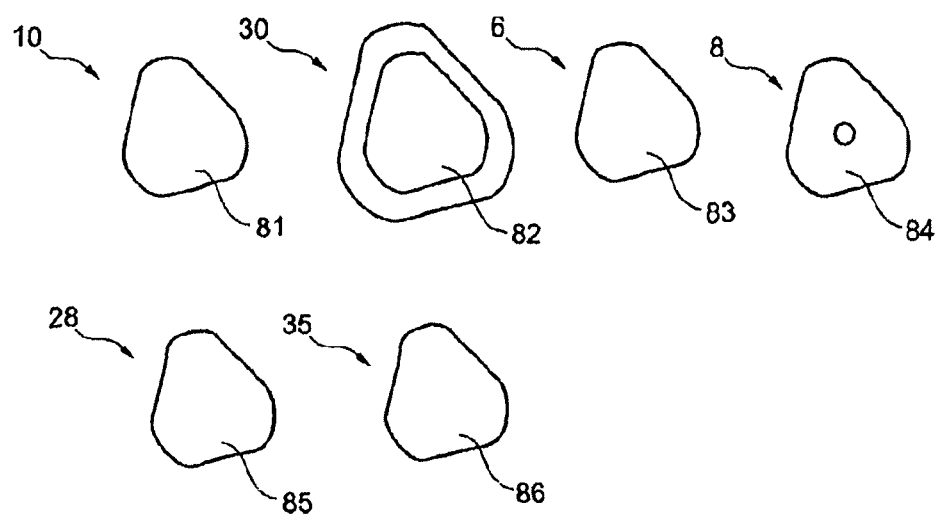
FIG. 8a-b shows an exemplifying embodiment of the cross-sectional profiles of the implant and the tools of the surgical kit.
Figure 8B:
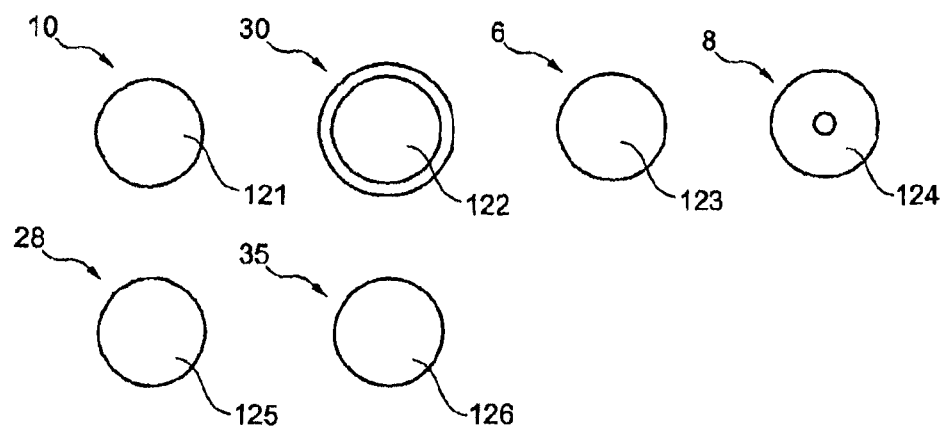

The cross-sectional profile 83 or 123, and thus the circumferential shape of the cutting edge 60, of the punch 6 corresponds to the chosen cross-section 81 or 121 of the implant surface 15 in size and shape (see FIG. 8*a-b*). The cross-sectional profile 83 or 123 of the punch varies in different realizations of the invention between 0.5 cm$^2$ and 20 cm$^2$, between 0.5 cm$^2$ and 15 cm$^2$, between 0.5 cm$^2$ and 10 cm$^2$ or preferably between about 1 cm$^2$ and 5 cm$^2$.

In one exemplifying embodiment of the invention the cartilage cutting tool is a cartilage cut drill 105. The cartilage cut drill 105 is used to cut the cartilage in the joint around the area of damaged cartilage to prepare for the insertion of the implant with a cut-drill technique.

The cartilage cut drill 105 is a drill, with a drill body in and with sharp cutting edges 108 and a center marker 106. The cartilage cut drill 105 has a cross-sectional profile that is designed to correspond to the inner cross-sectional profile 122 of the guide channel 54 with a tolerance enabling cartilage cut drill body 111 to slide within the guide channel 54. Also, the cross-sectional profile is designed to correspond to the cross-section of the implant.

The Reamer Guide

In one embodiment of the present invention the surgical kit comprises a reamer guide 28 that is placed in the guide channel 54 before reaming the recess in the bone (see FIG. 2 and FIG. 7*c-7d*, 8*a-8b*, 9*d*). The reamer guide 28 placed in the guide channel 54 protects the cartilage surrounding the implant site while the reamer bit 4 is used inside the guide channel 54 of the guide tool 12.

The reamer guide 28, see FIG. 7, is a channel shaped structure with thin walls designed to fit the inside of the guide channel 54, with a slight tolerance to allow a sliding movement of the reamer guide 28 in the guide channel 54. In other words, the cross sectional profile 85 of the reamer guide 28 fits the cross sectional profile 82 of the guide channel 54 such that the reamer guide 28 may be used as a lining, lining the insides of the guide channel 54 (see FIG. 8). The walls of the reamer guide 28 have a thickness of less than 1 mm. The reamer guide 28 preferably has a height 66 that is at least the height achieved by adding the inner height 31 of the guide channel 54 with the height 59 of the recess 5 of the punch 6. The reamer guide 28 is made from a material that can withstand the reamer tool and is inserted in the guide channel 54 to protect the cartilage in the surrounding hole which has been punched out. Examples of suitable materials are metals such as stainless steel or cobalt-chromium, polymer or ceramic materials.

The Drill-Guide

In one embodiment of the present invention the surgical kit comprises a drill guide 8 (see FIG. 2, 6*a-6b*, 8*a-8b*, 9*c*) that is used to direct a drill for drilling a hole in the bone at the site of cartilage damage, for fastening of the extending post 23 of the implant 10 in the bone tissue. The drill guide 8 comprises a drill guide body and a guide channel 7 passing through the drill guide body. The guide channel 7 is designed to receive and guide the drill during the surgical procedure. The drill guide 8 is designed to fit the inside of the guide channel 54, with a slight tolerance to allow a sliding movement of the drill guide 8 in the guide channel 54, see FIG. 8*a-b*. In other words, the cross-sectional profile of the drill guide body matches the cross-sectional profile of the guide channel 54 (see FIG. 8*a-b*). The fit ensures the correct, desired placement of the drill guide 8 on the cartilage surface and thus ensures the precise direction and placement of the drill hole in the bone.

The guide channel 7 is designed to be positioned in the drill guide body such that the position corresponds to the desired position of the drill hole in the bone. The positioning of the guide channel 7 in the drill guide 8 is coordinated with the positioning of the extending post 23 on the bone contacting surface 21 of the implant to ensure correct positioning of the implant in the bone. The material of the drill guide 8 is chosen from materials which can withstand the drill-bit rotation inside the drill channel 7 without wearing or losing its shape. Examples of such materials are metals or ceramic material. Further the drill guide 8 may be manufactured in a less wear resistant material and have a protective sealing inside the guide channel 7. The protective sealing can be made of a material resistant to drilling, for example a metal, such as stainless steel, or a ceramic material.

The length 62 of the drill guide 8 and thus the drill channel 7 is longer than the height 31 of the guide channel 54. The length is preferably 4-12 cm.

The cartilage contacting surface 64 of the drill guide 8 corresponds to the chosen implant surface 15 in size and shape. The surface 64 varies in different realizations of the invention between 0.5 cm$^2$ and 20 cm$^2$, between 0.5 cm$^2$ and 15 cm$^2$, between 0.5 cm$^2$ and 10 cm$^2$ or preferably between about 1 cm$^2$ and 5 cm$^2$. In one embodiment the cartilage contacting surface 64 of the drill guide 8 is designed to match the contour of the patient's cartilage and/or bone at the site of the joint where the implant is to be inserted.

Figure 9A:
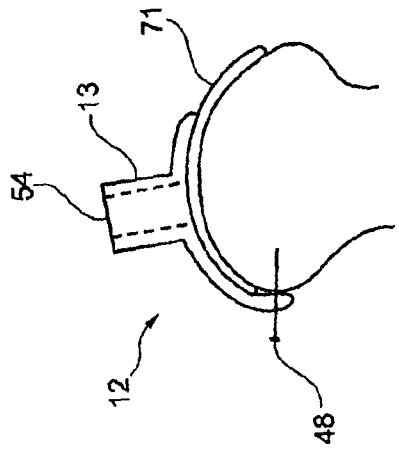
FIG. 9a-f shows an exemplifying embodiment of the surgical method using the surgical kit according to the invention.
Figure 9B:
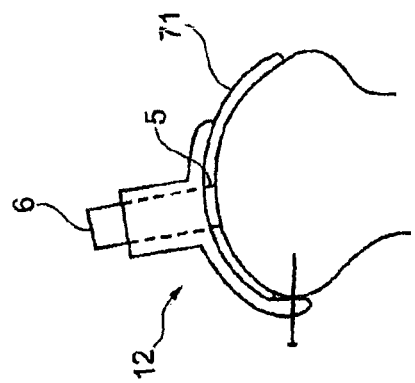
Figure 9C:
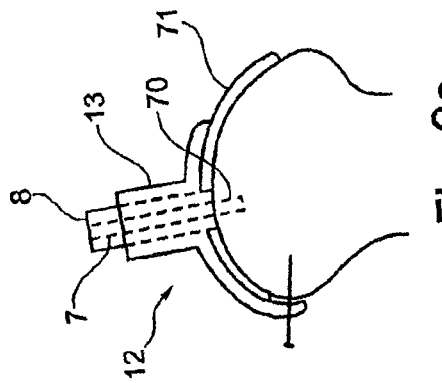
Figure 9D:
Figure 9E:
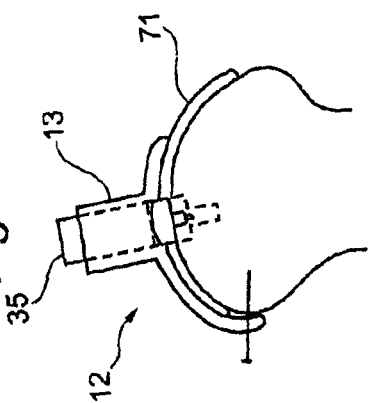
Figure 9F:
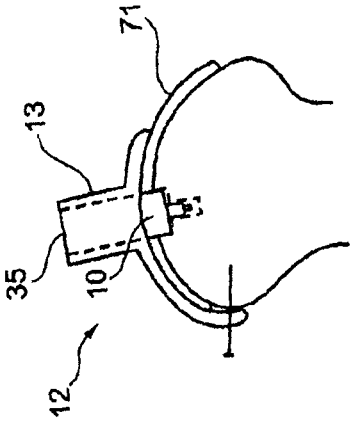
Figure 10:
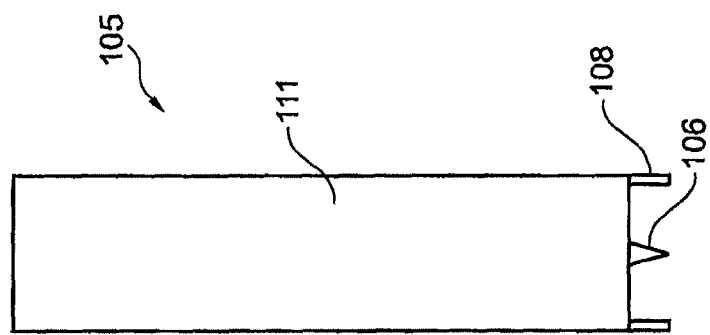
FIG. 10 shows an exemplifying embodiment of a cutting tool according to the present invention, a cutting drill

See FIG. 9*c* for a demonstration of how the drill-guide 8 fits inside the guide-channel 54 of the guide-tool 12.

Drill-Bit

The surgical kit of the present invention may also comprise a drill-bit 2 see FIGS. 2 and 7*a*. The drill-bit 2 have an adjustable depth gauge 1. The depth gauge 1 on the drill-bit 2 is supported by the top 30 of the guide channel 54 and by using this support the depth of the drill hole can be controlled. The drill-bit 2 fits inside the drill channel 7 in the drill-guide 8 to give drill-hole in the bone with an exact position and depth and where the depth is depending on the placement of the depth gauge 1 on the drill-bit 2, and also depending on the height of the guide-channel 31.

Death Adjustment Tool

Figure 12:
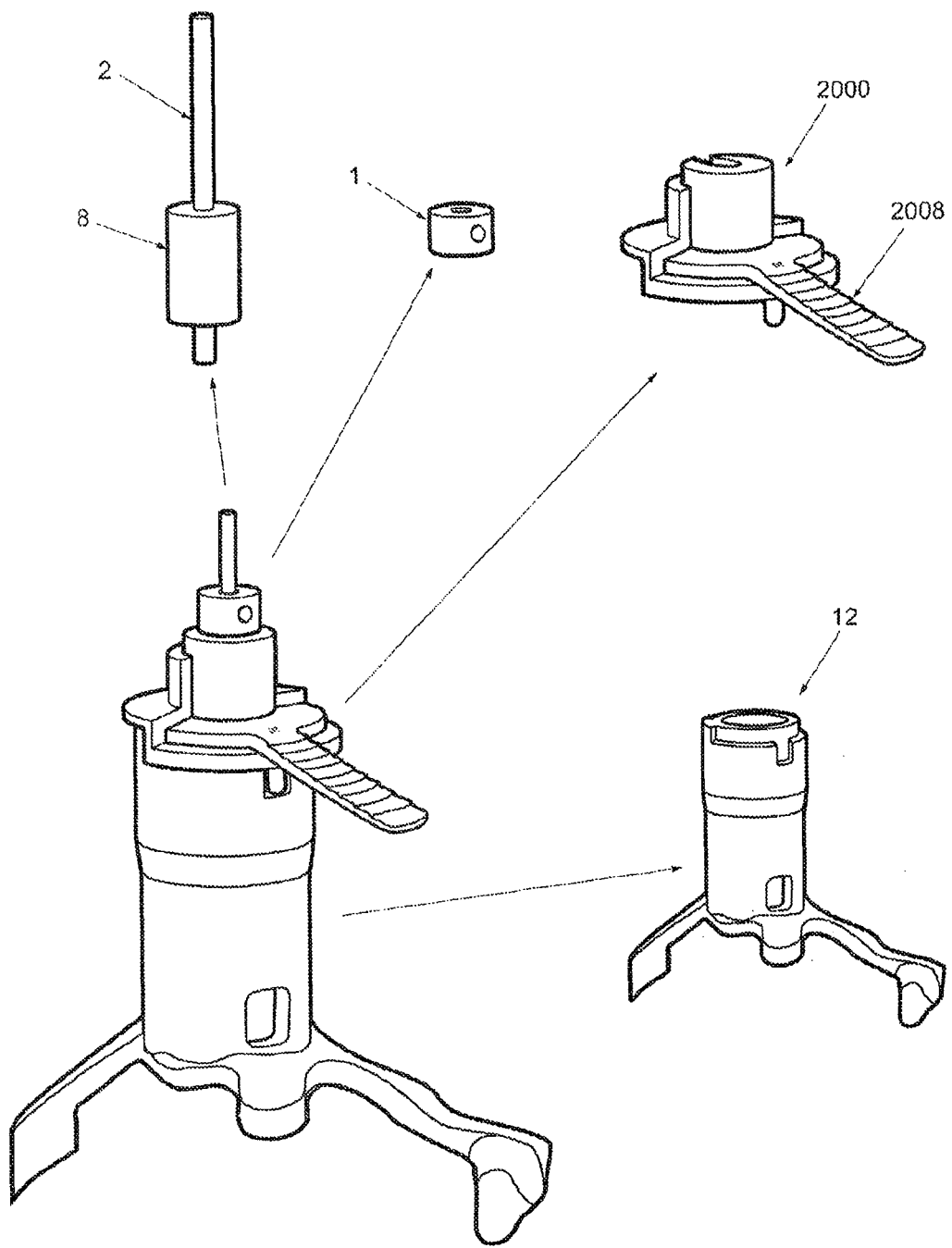
FIG. 12 shows an exemplifying embodiment of a drill depth adjustment tool placed on a guide tool together with a drill bit and a depth gauge and a drill guide according to the present invention
Figure 13:
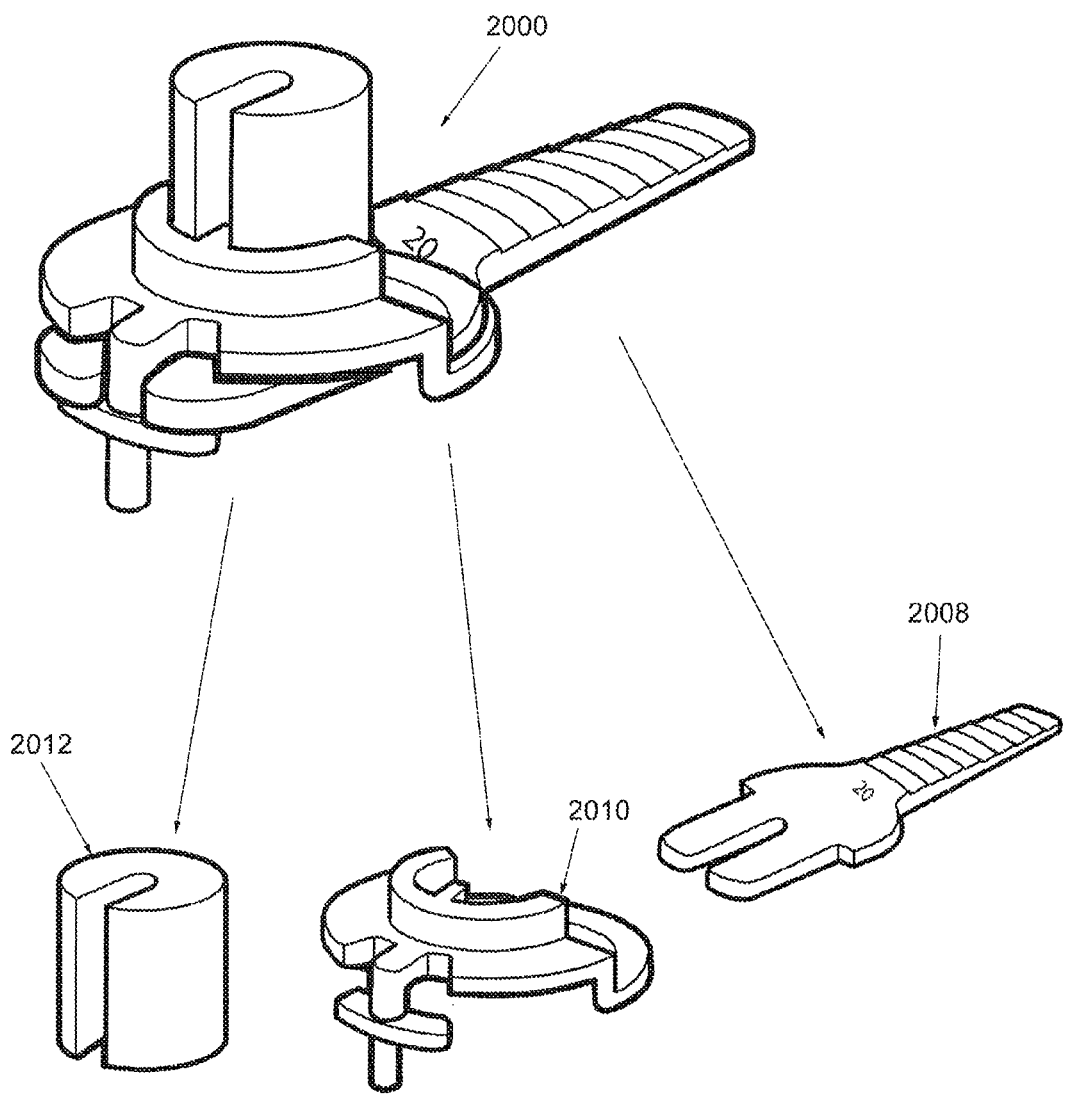
FIG. 13 shows an exemplifying embodiment of more details of the drill depth adjustment tool according to the present invention FIG. 14 A-B shows an exemplifying embodiment of how the drill depth adjustment tool may be used together with the drill guide and the guide tool.

The surgical kit of the present invention may also comprise a depth adjustment tool 2000, see FIG. 12 and FIG. 13. The depth adjustment tool 2000 according to the present invention comprises a drill depth bit 2012, a drill depth assembly holder 2010 and a drill depth spacer 2008.

Figure 14A:
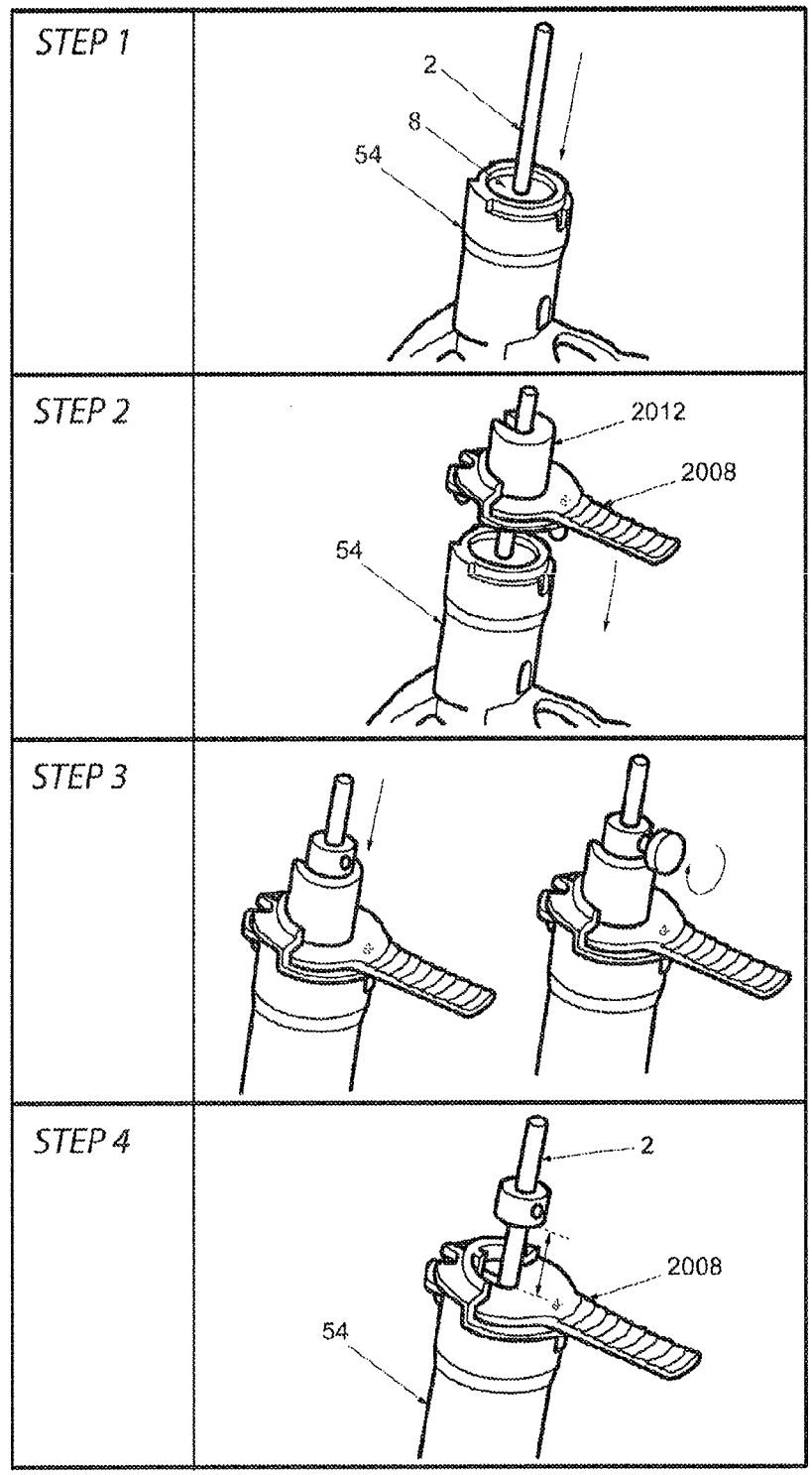
Figure 14B:
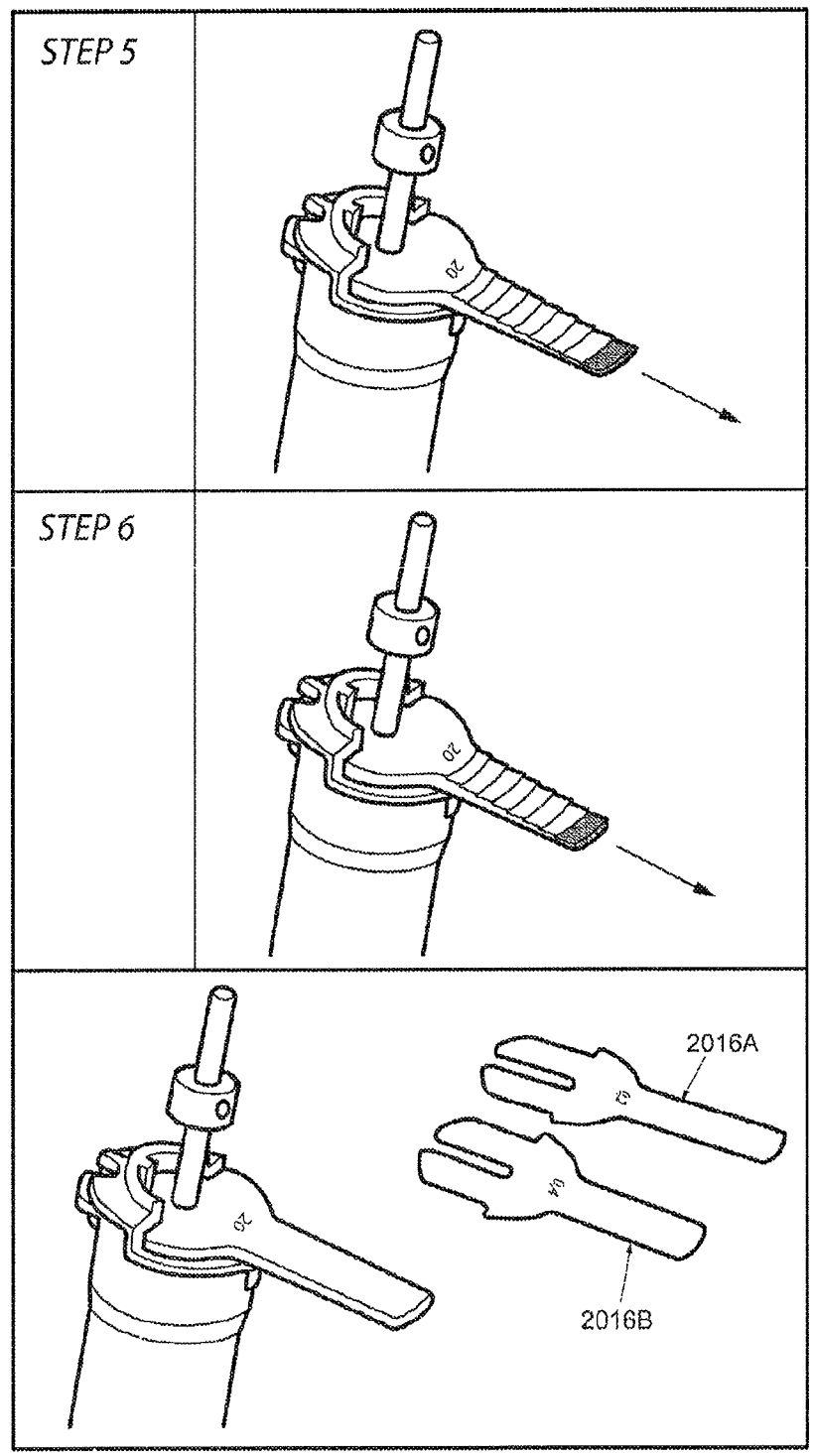

The depth adjustment tool 2000 according to the present invention may be used together with the drill guide 8 and the drill bit 2 comprising a drill depth gauge 1, see FIG. 14A-B.

In FIG. 14A-B an example of usage of the depth adjustment tool 2000 according to the present invention is shown.

Step 1 in FIG. 14A shows the drill guide 8 inserted together with the drill bit 2 inside the guide channel 54, of the guide tool 12. The drill bit 2 is inserted proximate to the underlying bone or cartilage.

In step 2 in FIG. 14A, the depth adjustment tool 2000 is placed onto the top of the guide channel 54 comprising the drill guide 8 and secured on the guide channel 54.

In step 3 in FIG. 14A, the drill depth gauge 1 of the depth adjustment tool 2000 is placed proximate to the drill depth bit 2012 and then attached to the drill-bit 2.

In step 4 in FIG. 14A the drill depth bit 2012, which determines the placement of the drill depth gauge 1 on the drill bit 2, is removed and then the drilling of the recess intended for the implant 10 or extending post 23 of the implant 10 may start.

The drill depth assembly holder 2010 holds the drill depth spacer 2008 which comprises several removable spacers 2016 of 0.1 micrometer to 1 mm thickness.

In step 5 in FIG. 14B, if the drill depth need to be further adjusted, the lowest spacer may be removed which allows the drill bit 2 to drill a deeper recess in the bone, the additional depth is depending on the thickness of the spacer 2016 or spacers (for example 2016A and 2016B) which is removed. Several spacers 2016 may be removed if a deeper recess is needed see for example step 6 in FIG. 14B.

Reamer-Bit

The surgical kit of the present invention may also comprise a reamer-bit, see FIGS. 2 and 7b. The reamer-bit 4 may have a depth gauge 3. The guide-tool 12 is used together with the reamer-bit 4, where the reamer-bit 4 is used inside the guide channel 54, removing bone tissue, aided by the guide channel 54. The depth gauge 3 on the reamer-bit 4 is supported the top 30 of the guide channel 54 and by using this support the depth of the reamed bone recess can be controlled. The depth of the reamed recess in the bone is depending on the placement of the depth gauge 3 on the reamer-bit 4, and also depending on the height 31 of the guide-channel 54. The depth of the reamed surface is determined depending on the injury and on the desired implants size.

Hammer Tool

The hammer tool 35 (see FIGS. 2 and 7e-f, 9f) consist of a solid body and is designed to fit the inside of the guide channel 54, with a slight tolerance to allow a sliding movement of the hammer tool 35 in the guide channel 54, see FIG. 8. The hammer tool 35 is used inside the guide channel 54 to hammer the implant in place. The height of the hammer tool 68 is the same height 62 as of the drill guide 8. Once the hammer tool is hammered in the same level as the top of the guide channel, the hammering and thus the placement of the implant is finished.

Detailed Description of a Method for Implanting the Implant Using the Set of Tools 1. Localize the area of the injury and determine the desired size and shape of the implant. The position and size of the cartilage damage can be identified by a combination of MRI or CT images or by dGEMRIC technique. The images may then be handled in special surgical planning tool software. All of the parts in the surgical kit may be individual adjusted depending on size of cartilage damage, location of the cartilage damage and also depending on a simulation of the individual surface-appearance without damage. Alternatively an implant from a set of predetermined implants may be selected and the set of tools designed or selected thereafter.

2. The implant to and set of tools of the invention are manufactured depending on; the size of the implant needed, the localization of the injury, the appearance of the cartilage surface intended to be replaced. The designs may be based on the MR images/CT-scanning images from the joint of the person having the cartilage damage, using the surgical planning software. The surgical planning software is connected to manufacturing devices, for example a laser printer, a lathe and/or a reamer, and the parts of the kit are manufactured using e.g. additive manufacturing, laser sintering techniques, turnery or reaming.

3. A surgical opening is made in the leg tissue depending on the localization of the injury and the size of the implant and also depending on the size and conformation of the guide tool.

4. The guide-tool 12 is placed on the surface of the knee cartilage, see FIG. 9. The guide-tool 12 fits due to the fact that it is custom made to be placed in that particular position. This allows the surgical procedure (cartilage and bone removal and insertion of the implant) to be performed with good accuracy and precision. If necessary the guide tool can be further stabilized with rivets on a part of the guide tool that is in contact with parts of the joint that have no cartilage tissue (see FIG. 9a).

5. After the guide tool 12 has been placed on the cartilage through an opening in the surrounding tissue, the cutting tool, e.g. punch 6, may optionally be used to punch or cut out a recess of the cartilage (see FIG. 9b). The cutting tool fits exactly in the guide channel 54 and thus can make a hole in the cartilage (71) of the desired size, depth, and with precision to fit the implant size and at the desired position.

6. The drill guide 8 is then inserted in the guide channel 54. The drill-bit 2 with an adjusted depth gauge 1 is used inside the drill channel 7 to give an exact, desired placement of the bore (70) in the bone where the extending post 23 of the implant 10 is to be attached. The hole is preferably made with a smaller diameter than the diameter 18 of the extending post 23 of the implant in so that when the implant 10 is hammered in place it will be firmly attached in the bone. The drill bit 2 and the drill guide 8 are removed after drilling. The drilling may alternatively be done before step 5 or after step 8.

7. A reamer guide 28 may optionally be placed in the guide channel 54 (see FIG. 9d).

8. The reamer bit 4 may be used to remove bone to fit the implant body 27. The reamer bit 4 and the depth gauge 3 of the reamer bit 4 are adjusted to make the desired depth of the reamer recess 73. The guide channel 54 of the guide tool 12 is used to aid the reamer 4 to ream out the desired shape and size from the bone in the joint and then the reamer guide is removed (see FIG. 9d).

The reaming and drilling steps 6 or 7-8 can alternatively be performed in the opposite order, i.e. reaming before drilling.

9. Lastly the guide-tool 12 is removed and the implant 10 is hammered in place in the exact matching hole made by the reamer and the drill.

Step 9 can alternatively be replaced by step 10.

10. The implant 10 is inserted in the guide channel 54 of the guide tool 12. A special designed hammer tool 30 is placed on top of the implant 10. A hammer is used to hammer the implant in position by hammering of the hammer guide 35 until the top of the hammer guide is in the same level as the top of the guide channel. After this the guide tool and hammer tool are removed (see FIGS. 9e and 9f).

The invention claimed is:

1. A surgical kit for cartilage repair at an articulating surface of a joint, comprising:
   a medical implant, comprising a substantially plate shaped implant body, wherein the plate shaped implant body has a predetermined cross-section that preferably substantially corresponds to the area of the damaged cartilage; and
   a set of tools with:
      a guide tool comprising a guide body with a guide channel, wherein the guide channel has a cross-sectional profile and a muzzle on the cartilage contact surface at a position corresponding to the site of the diseased cartilage; and
      an insert tool with a cross-sectional profile that is designed to correspond to the cross-sectional profile of the guide channel with a tolerance enabling the insert tool to slide within the guide channel,
   wherein said medical implant comprises an extending post having a cross-sectional area for securing the implant in a drilled hole of the bone, said guide tool comprising a positioning body and a guide body with a guide channel which goes through said positioning body and guide body,
   wherein the positioning body has a cartilage contact surface that is designed to fit the contour of the cartilage or subchondral bone in the joint in a predetermined area surrounding the site of diseased cartilage and wherein the cartilage contact surface is formed such that it uses the curvature in the cartilage surface in the joint for stability in order to give adequate support and stable positioning of the guide tool in the joint and at the same time maximum support and positional stability for the positioning body on the site of the injury compared to the cartilage contact surface and wherein the guide body is extending from a top surface.

2. The surgical kit of claim 1, wherein the insert tool is a drill guide with a cross-sectional profile that is designed to correspond to the cross-sectional profile of the guide channel with a tolerance enabling the drill guide to slide within the guide channel, and comprising a drill channel for guiding a drill bit, the drill channel being placed in a position that corresponds to the position of the extending post of the medical implant.

3. The surgical kit of claim 2, further comprising a drill bit with a cross-sectional area that is slightly smaller than the cross-sectional area of the extending post.

4. The surgical kit of claim 3, wherein the drill channel has a cross-sectional area that matches the cross-sectional area of the drill bit with a tolerance enabling the drill bit to slide within the drill channel.

5. The surgical kit of claim 3, wherein the drill bit is equipped with a depth gauge for adjustment of the depth of drilling.

6. The surgical kit of claim 1, wherein the insert tool is a reamer guide with a cross-sectional profile that is slightly smaller than the cross-sectional profile of the guide channel with a tolerance enabling the reamer guide to slide within the guide channel.

7. The surgical kit according to claim 1, wherein the insert tool is a cartilage cutting tool with a cross-sectional profile that is designed to correspond to the cross-sectional profile of the guide channel with a tolerance enabling the cartilage cutting tool to slide within the guide channel.

8. The surgical kit according to claim 7, wherein the cartilage cutting tool is a punch having an end with a cutting surface, said end having a recess with a cross-sectional profile that substantially corresponds to the cross-section of the plate shaped implant body.

9. The surgical kit according to claim 7, wherein the cartilage cutting tool is a cartilage cut drill having a cross-sectional profile that substantially corresponds to the cross-section of the plate shaped implant body.

10. The surgical kit of claim 1, further comprising a reamer bit.

11. The surgical kit of claim 10, wherein the reamer bit is equipped with a depth gauge for adjustment of the depth of reaming.

12. The surgical kit of claim 1, wherein the implant body of the implant is substantially flat, having a thickness of approximately 0.5-5 mm.

13. The surgical kit of claim 1, wherein the cartilage contact surface of the positioning body of the guide tool has three contacting points spread out around the guide body, for contacting parts of the joint in order to provide stable positioning of the guide tool in the joint.

14. The surgical kit of claim 1, wherein the guide channel has a height of 3-10 cm.

15. The surgical kit of claim 1, wherein the insert tool is a hammer tool with a cross-sectional profile that is designed to correspond to the cross-sectional profile of the guide channel with a tolerance enabling the hammer tool to slide within the guide channel.

16. The surgical kit of claim 5 further comprising a drill depth adjustment tool for adjustable drill depth adjustment.

17. The surgical kit of claim 16 wherein the drill depth adjustment tool comprises a drill depth bit and a drill depth assembly holder holding at least one drill depth spacer.

18. The surgical kit of claim 17 wherein the drill depth spacer comprises several spacers.

* * * * *